United States Patent [19]
Wu et al.

[11] Patent Number: 6,090,992
[45] Date of Patent: Jul. 18, 2000

[54] ISOMERIZATION CATALYST SYSTEM, METHOD OF MAKING AND METHOD OF USING SUCH CATALYST SYSTEM IN THE ISOMERIZATION OF SATURATED HYDROCARBONS

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 09/207,360

[22] Filed: Dec. 8, 1998

[51] Int. Cl.$^7$ .............. C07C 5/27; B01J 21/18; B01J 27/22
[52] U.S. Cl. .............. 585/748; 585/734; 585/747; 585/749; 585/750; 502/150; 502/152; 502/154; 502/170; 502/171; 502/174; 502/177; 502/224; 502/227; 502/228; 502/229; 502/230; 502/231; 502/169
[58] Field of Search .............. 502/174, 177, 502/224, 227, 228, 229, 230, 231, 150, 152, 154, 169, 170, 171; 585/734, 747, 748, 749, 750

[56] References Cited

U.S. PATENT DOCUMENTS

| | | |
|---|---|---|
| 4,219,445 | 8/1980 | Finch . |
| 4,325,843 | 4/1982 | Slaugh et al. . |
| 5,330,944 | 7/1994 | Sherif et al. .............. 502/64 |
| 5,451,389 | 9/1995 | Sherif .............. 423/439 |
| 5,536,692 | 7/1996 | Kubicek et al. .............. 502/230 |
| 5,576,466 | 11/1996 | Ledoux et al. .............. 585/735 |
| 5,776,852 | 7/1998 | Wu et al. .............. 502/177 |

OTHER PUBLICATIONS

Copending Application Serial No. 09/192,742 filed Nov. 16, 1998.

*Primary Examiner*—Elizabeth D. Wood
*Attorney, Agent, or Firm*—Jeffrey R. Anderson

[57] ABSTRACT

A catalyst system comprising alumina, at least one carburized transition metal, and at least one halogen component, and a method of preparing such catalyst system which comprises incorporating at least one transition metal compound into alumina thereby forming a transition metal-alumina compound; carburizing the transition metal-alumina compound thereby forming a carburized transition metal-alumina compound; and incorporating at least one halogen component into the carburized transition metal-alumina compound, are disclosed. The thus-obtained catalyst system is employed as a catalyst in the isomerization of a hydrocarbon feedstock comprising saturated hydrocarbons.

144 Claims, No Drawings

ISOMERIZATION CATALYST SYSTEM, METHOD OF MAKING AND METHOD OF USING SUCH CATALYST SYSTEM IN THE ISOMERIZATION OF SATURATED HYDROCARBONS

BACKGROUND OF THE INVENTION

This invention relates to catalyst systems useful in hydrocarbon upgrading processes and to methods of making and using such catalyst systems. In another aspect, this invention relates to processes for isomerizing hydrocarbons employing the novel catalyst systems of this invention.

It is known to isomerize saturated hydrocarbons in the presence of catalysts containing platinum and chlorine as described in the patent literature, e.g., in U.S. Pat. Nos. 5,004,859, 5,536,692, and 5,591,689.

One concern with using platinum-containing catalysts in the isomerization of saturated hydrocarbons is the sensitivity of platinum to poisons such as oxygen, nitrogen and sulfur. Therefore, it is desirable to develop catalyst systems which are less sensitive to such poisons than platinum-containing catalysts when used in the isomerization of saturated hydrocarbons.

SUMMARY OF THE INVENTION

It is an object of this invention to provide an improved process for isomerizing saturated hydrocarbons which is economical and efficient.

A further object of this invention is to provide a novel catalyst system which is useful for isomerizing saturated hydrocarbons and which is less sensitive to catalyst poisons such as oxygen, nitrogen and sulfur than platinum-containing isomerization catalysts.

A yet further object of this invention is to provide a method for making a novel catalyst system useful for isomerizing saturated hydrocarbons which is economical and efficient.

Yet another object of this invention is to employ this novel catalyst system as a catalyst in the isomerization of saturated hydrocarbons.

The inventive catalyst system comprises alumina, at least one carburized transition metal and at least one halogen component. The inventive catalyst system can be prepared by:

incorporating at least one transition metal compound into alumina thereby forming a transition metal-alumina compound;

carburizing the transition metal-alumina compound thereby forming a carburized transition metal-alumina compound; and incorporating at least one halogen component into the carburized transition metal-alumina compound thereby forming the inventive catalyst system.

The inventive catalyst system can be used in the isomerization of saturated hydrocarbons by contacting, under isomerization conditions, a hydrocarbon feedstock with the inventive catalyst system.

Other objects and advantages of the invention will become apparent from the detailed description and the appended claims.

DETAILED DESCRIPTION OF THE INVENTION

Any suitable alumina material can be used in preparing the inventive catalyst system. Suitable aluminas include (but are not limited to) hydrated aluminas (such as boehmite, pseudoboehmite, bayerite), alpha-alumina, beta-alumina, gamma-alumina, delta-alumina, eta-alumina and theta-alumina, preferably gamma-alumina. The alumina material generally has a surface area (determined by the BET method of Brunauer, Emmett and Teller employing $N_2$) of about 100 to about 400 $m^2/g$, a pore volume (measured by nitrogen intrusion porosimetry) of about 0.2 to about 1.0 $cm^3/g$, and a particle size of about 8 to about 200 mesh.

At least one transition metal compound can be incorporated into the alumina by any suitable means or method known in the art for incorporating metallic elements into a substrate material thereby forming a transition metal-alumina compound.

Examples of suitable transition metal compounds include, but are not limited to, ammonium polytungstate, ammonium paratungstate, ammonium tetrathiotungstate (VI), bis(cyclopentadienyl)tungsten dichloride, bis(i-propylcyclopentadienyl)tungsten dihydride, cyclopentadienyltungsten tricarbonyl dimer, mesitylene tungsten tricarbonyl, tungsten (IV) chloride, tungsten (VI) chloride, tungstic acid, 12-tungstophosphoric acid hydrate, titanium (IV) bromide, titanium (IV) n-butoxide, titanium (IV) t-butoxide, titanium (IV) chloride, titanium (di-i-propoxide) bis(acetylacetonate), titanium (IV) ethoxide, titanium (IV) 2-ethylhexoxide, titanium (IV) i-propoxide, tris (2,2,6,6-tetramethyl-3,5-heptanedionato)titanium (III), zirconium (IV) bromide, zirconium (IV) n-butoxide, zirconium (IV) t-butoxide, zirconium (IV) chloride, zirconium (IV) dichloride oxide hydrate, zirconium (IV) dinitrate oxide hydrate, zirconium (IV) ethoxide, hafnium (IV) chloride, hafnium (IV) dichloride oxide octahydrate, hafnium (IV) ethoxide, hafnium (IV) i-propoxide monoisopropylate, vanadium (III) chloride, vanadium (V) trichloride oxide, vanadium (V) tri-i-propoxy oxide, niobium (V) bromide, niobium (V) chloride, niobium (V) ethoxide, tantalum (V) chloride, tantalum (V) ethoxide, tantalum (V) methoxide, chromium (III) acetate, chromium (III) acetylacetonate, chromium (III) bromide hexahydrate, chromium (III) chloride, chromium (III) 2-ethylhexanoate, chromium (III) naphthenate, chromium (III) nitrate nonahydrate, chromium (III) sulfate hydrate, ammonium molybdate tetrahydrate, molybdenum (II) acetate dimer, molybdenum carbonyl, molybdenum (V) chloride, molybdenum (VI) dioxide bis(acetylacetonate), 12-molybdophosphoric acid hydrate and combinations of any two or more thereof.

It is preferred to use any standard incipient wetness technique for impregnating the alumina with the at least one transition metal compound. A preferred method uses a liquid impregnation solution containing the desirable concentration of the at least one transition metal compound. It is particularly desirable to use an aqueous solution formed by dissolving the at least one transition metal compound in water. It is preferable to use an acidic solution to aid in the dissolution of the at least one transition metal compound. The acid used to acidify the impregnation solution is preferably citric acid.

The transition metal-alumina compound can then be shaped by any suitable means or method such as by pelletizing, extruding or tableting. The presently preferred method is extrusion of the transition metal-alumina compound into cylindrical extrudates.

Generally, the extruded transition metal-alumina compound is calcined prior to further treatment. The calcination temperature is generally in the range of from about 300° C. to about 1000° C., preferably from about 350° C. to about 750° C., and most preferably from 450° C. to 650° C. and a pressure in the range of from about 0.5 to about 50 atmospheres (atm), preferably from about 0.5 to about 30 atm, and most preferably from 0.5 to 10 atm. The calcination can be performed in either an air atmosphere or an inert atmosphere or a combination thereof for a time period in the range of from about 0.1 hour to about 30 hours, preferably from about 2 hours to about 20 hours, and most preferably from 3 hours to 15 hours.

The calcined, extruded transition metal-alumina compound can be carburized under conditions suitable for converting at least a portion of the transition metal to a carburized transition metal. Preferably, the carburized transition metal is of the formula $X_2C$, wherein X is the transition metal and C is carbon. The carburization conditions more particularly include a temperature in the range of from about 300° C. to about 1,500° C., preferably from about 400° C. to about 1,200° C., and most preferably from 500° C. to 1,000° C. The carburization is preferably performed in the presence of a gas comprising methane and hydrogen for a time period in the range of from about 0.1 hour to about 30 hours, preferably from about 2 hours to about 20 hours, and most preferably from 3 hours to 15 hours.

It is believed that carburization of the at least one transition metal compound enhances the catalytic activity of the catalyst system and decreases the catalyst system's sensitivity to poisons such as oxygen, nitrogen and sulfur.

The preferred carburized transition metal is carburized tungsten, even more preferably, ditungsten carbide of the formula $W_2C$, wherein W is tungsten and C is carbon.

The carburized transition metal-alumina compound is contacted with at least one halogen component. Examples of suitable halogen components include, but are not limited to, aluminum chloride, ethyl aluminum dichloride, methylaluminum dichloride, methylaluminum sesquichloride, dimethylaluminum chloride, ethylaluminum sesquichloride, diethylaluminum chloride, and mixtures or combinations of any two or more thereof. Presently preferred are ethylaluminum dichloride and aluminum chloride.

These halogen components are easily hydrolyzed and thus should be handled and applied in a dry environment. Preferably, they are dissolved in a dry organic hydrocarbon solvent, such as in a $C_6$ to $C_{10}$ cycloalkane, benzene, toluene, ethylbenzene, xylene(s), and the like. The presently preferred solvent is cyclohexane. The solution containing the at least one halogen component and the hydrocarbon solvent is then contacted with the carburized transition metal-alumina compound to incorporate the at least one halogen component into the carburized transition metal-alumina compound.

Another method of contacting the carburized transition metal-alumina compound with such at least one halogen component includes placing the carburized transition metal-alumina compound in a contactor directly above a quantity of the at least one halogen component, which is preferably in solid form, heating the contactor contents to a temperature in the range of from about 500° C. to about 1,000° C., so as to vaporize the at least one halogen component, and passing a helium gas stream up through the at least one halogen component first and then through the tungsten carbide-alumina compound for a time period in the range of from about 1 hour to about 30 hours. The at least one halogen component is sublimed into the helium gas stream and then deposited into the interstitial spaces of the carburized transition metal-alumina compound.

The resulting material can then be calcined to form the inventive catalyst system. The calcination conditions are generally as described above.

Generally, the amount of elemental transition metal (which is contained in the at least one carburized transition metal) present in the inventive catalyst system is in the range of from greater than about 0 to about 40 weight %, preferably in the range of from about 1 weight % to about 35 weight %, and most preferably from 5 weight % to 30 weight % based on the total weight of the inventive catalyst system, measured on an elemental transition metal basis.

Generally, the amount of halogen present in the inventive catalyst system is in the range of from greater than about 0 to about 40 weight %, preferably from about 0.5 weight % to about 25 weight %, and most preferably from 0.5 weight % to 10 weight % based on the total weight of the inventive catalyst system, measured on an elemental halogen basis.

All weight percents of components of the inventive catalyst system can be measured using X-ray fluorescence analysis, as described in "Spectrometry: Principles and Practices in X-ray Spectrometric Analysis" by Eugene Burton, 2nd edition.

The inventive catalyst system is generally employed in the isomerization of a hydrocarbon feedstock comprising saturated hydrocarbons (preferably normal alkanes). Examples of suitable hydrocarbon feedstocks include, but are not limited to, normal butane, normal pentane, normal hexane, normal heptane, normal octane, cyclohexane, methylpentane, methylcyclopentane, dimethylcyclopentane, cycloheptane, methylcyclohexane, methylcycloheptane and the like, and mixtures or combinations of any 2 or more thereof.

Generally, hydrogen is mixed with the hydrocarbon feedstock to form a feed mixture which is contacted with the inventive catalyst system contained in an isomerization zone. The concentration of the hydrogen in the feed mixture during this contacting step shall be such as to provide a hydrogen to saturated hydrocarbon molar ratio of at least about 0.01:1, preferably in the range of from about 0.01:1 to about 5:1, and most preferably in the range of from 0.02:1 to 2:1. The hydrocarbon feedstock and hydrogen can be contacted with the inventive catalyst system by any suitable manner. The contacting step can be operated as a batch process step or, preferably, as a continuous process step. In the latter operation, a solid catalyst bed or a moving catalyst bed or a fluidized catalyst bed can be employed. Any of these operational modes has advantages and disadvantages, and those skilled in the art can select the one most suitable for a particular feed and catalyst system.

The contacting step is preferably carried out within an isomerization zone, wherein is contained the inventive catalyst system, and under reaction conditions that suitably promote isomerization of at least a portion of the saturated hydrocarbons of the hydrocarbon feedstock. The reaction temperature of the isomerization zone is more particularly in the range of from about 80° C. to about 260° C., preferably in the range of from about 90° C. to about 200° C., and most preferably in the range of from 100° C. to 150° C. The contacting pressure of the isomerization zone is within the range of from about atmospheric to about 1500 psig, preferably in the range of from about 250 psig to about 1000 psig, and most preferably in the range of from 300 psig to 750 psig.

The flow rate at which the hydrocarbon feedstock is charged to the isomerization zone is such as to provide a weight hourly space velocity ("WHSV") in the range of from exceeding 0 hour$^{-1}$ upwardly to about 1000 hour$^{-1}$. The term "weight hourly space velocity", as used herein, shall mean the numerical ratio of the rate at which a hydrocarbon feedstock is charged to the isomerization zone in pounds per hour divided by the pounds of catalyst contained in the isomerization zone to which the hydrocarbon feedstock is charged. The preferred WHSV of the hydrocarbon feedstock to the isomerization zone is preferably in the range of from about 0.25 hour$^{-1}$ to about 250 hour$^{-1}$ and, most preferably, in the range of from 0.5 hour$^{-1}$ to 100 hour$^{-1}$.

In order to activate the catalyst and to retard its deactivation during the isomerization reaction, chloride is frequently added to the feed mixture in an amount such that the chloride is present in the feed mixture in the range of from about 0.001 to about 1 weight % based on the total weight of the feed mixture. The chloride is generally in the form of at least one chloroalkane, preferably carbon tetrachloride, chloroform, ethylchloride or isopropylchloride.

The following examples are presented to further illustrate the invention and are not to be construed as unduly limiting its scope.

EXAMPLE I

This example illustrates the preparation of catalysts which were subsequently tested as catalysts in the isomerization of n-butane to iso-butane.

Tungsten-impregnated Alumina

A 25 gram quantity of a commercially available alumina (provided by Vista Chemical Company, Houston, Tex., under product designation Catapal® D alumina) was impregnated, by incipient wetness, with an aqueous solution containing 7.8 grams of ammonium paratungstate, 7.8 grams of citric acid and 23.3 grams of water. The thus obtained impregnated alumina was extruded followed by calcining at 538° C. for 2 hours.

Catalyst A (control)

A 23.6 gram quantity of the above-described tungsten-impregnated alumina was carburized by passing methane and hydrogen gas streams over the tungsten-impregnated alumina at flow rates of 100 ml/min and 400 ml/min, respectively, at a temperature of 750° C. for 6 hours.

Catalyst B (invention)

A 10.9 gram quantity of Catalyst A was contacted with a solution containing 1.2 grams of ethyl aluminum dichloride (EADC) and 5.0 grams of cyclohexane. The thus-treated material was subsequently calcined at a temperature of 650° C. for 6 hours.

Catalyst C (control)

An 11.8 gram quantity of the above-described tungsten-impregnated alumina was contacted with a solution containing 1.3 grams of EADC and 5.4 grams of cyclohexane. The thus-treated material was calcined at a temperature of 650° C. for 6 hours.

Catalyst D (control)

A 50 gram quantity of a commercially available alumina (provided by United Catalysts, Inc., Louisville, Ky., under product designation "CS-331-4") was calcined at a temperature of 538° C. for 6 hours followed by heat treatment at a temperature of 120° C. for 64 hours. The calcined alumina was placed in a quartz calcine tube as a fixed bed directly above about a 3.5 gram quantity of solid aluminum chloride. The calcined alumina and aluminum chloride were heated to a temperature of 650° C. and a 300 ml/min helium gas stream was passed upwardly through the aluminum chloride and the calcined alumina for a time period of 6 hours.

Catalyst E (invention)

A 12.2 gram quantity of a commercially available alumina (provided by United Catalyst, Inc., Louisville, Ky., under product designation "CS-331-4") was impregnated, by incipient wetness, with an aqueous solution containing 2.2 grams of ammonium paratungstate, 2.2 grams of citric acid and 6.4 grams of water. The thus-obtained tungsten-impregnated alumina was calcined at 538° C. for 6 hours.

The thus-obtained calcined, tungsten-impregnated alumina was carburized by passing methane and hydrogen gas streams over the calcined, tungsten-impregnated alumina at flow rates of 100 ml/min and 400 ml/min, respectively, at a temperature of 750° C. for 6 hours.

The thus-obtained tungsten carbide-alumina was placed in a quartz calcine tube as a fixed bed directly above a 3.5 gram quantity of solid aluminum chloride. The tungsten carbide-alumina and aluminum chloride were heated to a temperature of 650° C. and a 300 ml/min helium gas stream was passed upwardly through the aluminum chloride and the tungsten carbide-alumina for a time period of 6 hours.

Catalyst F (control)

A 12.2 gram quantity of a commercially available alumina (provided by United Catalyst, Inc., Louisville, Ky., under product designation "CS-331-4") was impregnated, by incipient wetness, with an aqueous solution containing 2.2 grams of ammonium paratungstate, 2.2 grams of citric acid and 6.4 grams of water. The thus-obtained tungsten-impregnated alumina was calcined at 538° C. for 6 hours.

The thus-obtained tungsten-impregnated alumina was placed in a quartz calcine tube as a fixed bed directly above a 3.6 gram quantity of solid aluminum chloride. The tungsten-impregnated alumina and aluminum chloride were heated to a temperature of 650° C. and a 300 ml/min helium gas stream was passed upwardly through the aluminum chloride and the tungsten-impregnated alumina for a time period of 6 hours.

EXAMPLE II

This example illustrates the use of the catalysts described in Example I in the isomerization of n-butane.

For each of Runs 1 through 6, a 5 ml sample of the catalyst materials described in Example I, that is, Catalysts A, B, C, D, E, and F, respectively, was placed into a stainless steel tube reactor (length: about 18 inches; inner diameter: about 0.5 inches). The steel reactor tube was heated to about 110° C. A stream of hydrogen gas was passed through the catalyst bed at a rate of 12.0 liters/hour. The reactor pressure was about 500 psig. Liquid n-butane was introduced at a rate of 6.0 liters/hour while the flow of hydrogen gas was maintained at 12.0 liters/hour so as to provide a mole ratio of hydrogen to n-butane of about 2.2:1. Carbon tetrachloride was injected into the feed mixture at a rate of 0.89 microliters/hour. The isomerization product was analyzed by means of a gas chromatograph. Test results for Runs 1 through 6 for Catalysts A, B, C, D, E, and F. respectively, are summarized in the Table. All test data were obtained after 7 hours on stream.

TABLE

| Run | Catalyst | Isobutane in Product, weight % | Isobutane Selectivity, % |
|---|---|---|---|
| 1 | A (Catapal ® D + AP/CA + EX + C + CB) (control) | 0 | — |
| 2 | B (Catapal ® D + AP/CA + EX + C + CB + EADC + C) (invention) | 11.9 | 99.3 |
| 3 | C (Catapal ® D + AP/CA + EX + C + EADC + C) (control) | 0 | — |

TABLE-continued

| Run | Catalyst | Isobutane in Product, weight % | Isobutane Selectivity, % |
|---|---|---|---|
| 4 | D (CS-331-4 + C + D + AlCl₃ + C) (control) | 0 | — |
| 5 | E (CS-331-4 + AP/CA + C + CB + AlCl₃ + C) (invention) | 10.4 | 99.3 |
| 6 | F (CS-331-4 + AP/CA + C + AlCl₃ + C) (control) | 0 | — |

Catapal ® D = Alumina supplied by Vista Chemical Company, Houston, Texas
AP = Ammonium Paratungstate
CA = Citric Acid
EX = Extrude
C = Calcine
CB = Carburize
EADC = Ethyl Aluminum Dichloride Treatment
CS-331-4 = Alumina supplied by United Catalysts, Inc., Louisville, Kentucky
D = Drying at 120° C. for 64 hours
AlCl₃ = Treatment with Aluminum Chloride The test data presented in the Table show that the inventive catalysts B and E used in Runs 2 and 5 were significantly more active in n-butane isomerization than control catalysts A, C, D, and F used in Runs 1, 3, 4, and 6.

Control Runs 1, 3, 4 and 6 demonstrated that catalysts A, C, D and F were ineffective in n-butane isomerization.

Additionally, the percent iso-butane in product for inventive catalysts B and E used in Runs 2 and 5 are comparable to the percent iso-butane in product for typical platinum-containing isomerization catalysts, which range from about 6 weight % to about 18 weight % isobutane in product, as presented in examples in U.S. Pat. No. 5,536,692 at column 6 and U.S. Pat. No. 5,591,689 at column 8.

The test data in the Table also show that the conversion selectivity to isobutane resulting from the conversion of n-butane in Runs 2 and 5 were extremely high, both at 99.3%. The selectivity to isobutane is defined as 100 times the weight of isobutane in the product divided by the difference in the weight of the product and the weight of n-butane contained in the product.

Thus, use of the inventive transition metal carbide-containing isomerization catalysts result in n-butane conversions to isobutane comparable to that for platinum-containing isomerization catalysts but with a decreased sensitivity to poisons such as oxygen, nitrogen and sulfur as compared to the platinum-containing isomerization catalysts.

Reasonable variations, modifications, and adaptations can be made within the scope of the disclosure and the appended claims without departing from the scope of this invention.

That which is claimed is:

1. A catalyst system comprising alumina, at least one carburized transition metal, and at least one halogen component.

2. A catalyst system as recited in claim 1 wherein said at least one halogen component comprises chlorine.

3. A catalyst system as recited in claim 1 wherein said at least one carburized transition metal is of the formula $X_2C$, wherein X is a transition metal and C is carbon.

4. A catalyst system as recited in claim l wherein said at least one carburized transition metal comprises a transition metal selected from the group consisting of titanium, zirconium, hafnium, vanadium, niobium, tantalum, chromium, molybdenum, tungsten and combinations of any two or more thereof in an amount in the range of from greater than about 0 weight % to about 50 weight % based on the total weight of said catalyst system.

5. A catalyst system as recited in claim 1 wherein the halogen of said at least one halogen component is present in an amount in the range of from greater than about 0 weight % to about 50 weight % based on the total weight of said catalyst system.

6. A catalyst system as recited in claim 1 wherein said at least one carburized transition metal is carburized titanium.

7. A catalyst system as recited in claim 1 wherein said at least one carburized transition metal is carburized zirconium.

8. A catalyst system as recited in claim 1 wherein said at least one carburized transition metal is carburized hafnium.

9. A catalyst system as recited in claim 1 wherein said at least one carburized transition metal is carburized vanadium.

10. A catalyst system as recited in claim 1 wherein said at least one carburized transition metal is carburized niobium.

11. A catalyst system as recited in claim 1 wherein said at least one carburized transition metal is carburized tantalum.

12. A catalyst system as recited in claim 1 wherein said at least one carburized transition metal is carburized chromium.

13. A catalyst system as recited in claim 1 wherein said at least one carburized transition metal is carburized molybdenum.

14. A catalyst system as recited in claim 1 wherein said at least one carburized transition metal is carburized tungsten.

15. A catalyst system as recited in claim 1 which has been calcined.

16. A catalyst system as recited in claim 1 which has been calcined, wherein the calcining of said catalyst system is conducted at a temperature in the range of from about 300° C. to about 1000° C. and for a time period of from about 0.1 hour to about 30 hours.

17. A method of preparing a catalyst system comprising the steps of:

incorporating at least one transition metal compound into alumina thereby forming a transition metal-alumina composition;

carburizing said transition metal-alumina composition thereby forming a carburized transition metal-alumina composition; and incorporating at least one halogen component into said carburized transition metal-alumina composition thereby forming said catalyst system.

18. A method as recited in claim 17 wherein said step of incorporating said at least one transition metal compound into said alumina includes mixing said alumina with a solution containing said at least one transition metal compound and an acid.

19. A method as recited in claim 18 wherein said acid is citric acid.

20. A method as recited in claim 17 wherein said transition metal-alumina composition is calcined at a temperature in the range of from about 300° C. to about 1000° C. and for a time period of from about 0.1 hour to about 30 hours prior to said carburizing step.

21. A method as recited in claim 17 wherein said at least one transition metal compound comprises a compound selected from the group consisting of ammonium polytungstate, ammonium paratungstate, ammonium tetrathiotungstate (VI), bis(cyclopentadienyl)tungsten dichloride, bis(i-propylcyclopentadienyl)tungsten dihydride, cyclopentadienyltungsten tricarbonyl dimer, mesitylene tungsten tricarbonyl, tungsten (IV) chloride, tungsten (VI) chloride, tungstic acid, 12-tungstophosphoric acid hydrate, titanium (IV) bromide, titanium (IV) n-butoxide, titanium (IV) t-butoxide, titanium (IV) chloride, titanium (di-i-propoxide)bis(acetylacetonate), titanium (IV) ethoxide, titanium (IV) 2-ethylhexoxide, titanium (IV) i-propoxide, tris (2,2,6,6-tetramethyl-3,5-heptanedionato) titanium (III), zirconium (IV) bromide, zirconium (IV) n-butoxide, zirconium (IV) t-butoxide, zirconium (IV) chloride, zirconium (IV) dichloride oxide hydrate, zirconium (IV) dinitrate oxide hydrate, zirconium (IV) ethoxide, hafnium (IV) chloride, hafnium (IV) dichloride oxide octahydrate, hafnium (IV) ethoxide, hafnium (IV) i-propoxide monoisopropylate, vanadium (III) chloride, vanadium (V) trichloride oxide, vanadium (V) tri-i-propoxy oxide, niobium (V) bromide, niobium (V) chloride, niobium (V) ethoxide, tantalum (V) chloride, tantalum (V) ethoxide, tantalum (V) methoxide, chromium (III) acetate, chromium (III) acetylacetonate, chromium (III) bromide hexahydrate, chromium (III) chloride, chromium (III) 2-ethylhexanoate, chromium (III) naphthenate, chromium (III) nitrate nonahydrate, chromium (III) sulfate hydrate, ammonium molybdate tetrahydrate, molybdenum (II) acetate dimer, molybdenum carbonyl, molybdenum (V) chloride, molybdenum (VI) dioxide bis(acetylacetonate), 12-molybdophosphoric acid hydrate and combinations of any two or more thereof.

22. A method as recited in claim 17 wherein said carburizing step comprises heating said transition metal-alumina composition at a temperature in the range of from about 300° C. to about 1500° C. in the presence of methane and hydrogen.

23. A method as recited in claim 17 wherein said at least one halogen component comprises chlorine.

24. A method as recited in claim 17 wherein said step of incorporating said at least one halogen component comprises contacting said carburized transition metal-alumina composition with a compound selected from the group consisting of aluminum chloride, ethyl aluminum dichloride, methylaluminum dichloride, methylaluminum sesquichloride, dimethylaluminum chloride, ethylaluminum sesquichloride, diethylaluminum chloride, and combinations of any two or more thereof to form said catalyst system.

25. A method as recited in claim 17 wherein said step of incorporating said at least one halogen component into said carburized transition metal-alumina composition includes:
mixing said carburized transition metal-alumina composition with said at least one halogen component; and
calcining the resulting mixture at a temperature in the range of from about 300° C. to about 1000° C. and for a time period of from about 0.1 hour to about 30 hours thereby forming said catalyst system.

26. A method as recited in claim 17 wherein said step of incorporating said at least one halogen component into said carburized transition metal-alumina composition includes:
vaporizing said at least one halogen component; incorporating said vaporized at least one halogen component into said carburized transition metal-alumina composition; and
calcining the resulting mixture at a temperature in the range of from about 300° C. to about 1000° C. and for a time period of from about 0.1 hour to about 30 hours thereby forming said catalyst system.

27. A method as recited in claim 17 wherein said catalyst system comprises a transition metal selected from the group consisting of titanium, zirconium, hafnium, vanadium, niobium, tantalum, chromium, molybdenum, tungsten and combinations of any two or more thereof in an amount in the range of from greater than about 0 weight % to about 50 weight % based on the total weight of said catalyst system.

28. A method as recited in claim 17 wherein said catalyst system contains halogen in an amount in the range of from greater than about 0 weight % to about 50 weight % based on the total weight of said catalyst system.

29. A method as recited in claim 17 wherein said at least one carburized transition metal is carburized titanium.

30. A method as recited in claim 17 wherein said at least one carburized transition metal is carburized zirconium.

31. A method as recited in claim 17 wherein said at least one carburized transition metal is carburized hafnium.

32. A method as recited in claim 17 wherein said at least one carburized transition metal is carburized vanadium.

33. A method as recited in claim 17 wherein said at least one carburized transition metal is carburized niobium.

34. A method as recited in claim 17 wherein said at least one carburized transition metal is carburized tantalum.

35. A method as recited in claim 17 wherein said at least one carburized transition metal is carburized chromium.

36. A method as recited in claim 17 wherein said at least one carburized transition metal is carburized molybdenum.

37. A method as recited in claim 17 wherein said at least one carburized transition metal is carburized tungsten.

38. A catalyst system prepared by the method of claim 20.
39. A catalyst system prepared by the method of claim 22.
40. A catalyst system prepared by the method of claim 23.
41. A catalyst system prepared by the method of claim 24.
42. A catalyst system prepared by the method of claim 25.
43. A catalyst system prepared by the method of claim 26.
44. A catalyst system prepared by the method of claim 27.
45. A catalyst system prepared by the method of claim 28.

46. A process for isomerizing saturated hydrocarbons comprising contacting a hydrocarbon feed comprising at least one saturated hydrocarbon under isomerization conditions with the catalyst system of claim 1.

47. A process as recited in claim 46 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

48. A process as recited in claim 47 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

49. A process for isomerizing saturated hydrocarbons comprising contacting a hydrocarbon feed comprising at least one saturated hydrocarbon under isomerization conditions with the catalyst system of claim 2.

50. A process as recited in claim 49 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

51. A process as recited in claim 50 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

52. A process for isomerizing saturated hydrocarbons comprising contacting a hydrocarbon feed comprising at least one saturated hydrocarbon under isomerization conditions with the catalyst system of claim 3.

53. A process as recited in claim 52 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

54. A process as recited in claim 53 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

55. A process for isomerizing saturated hydrocarbons comprising contacting a hydrocarbon feed comprising at least one saturated hydrocarbon under isomerization conditions with the catalyst system of claim 4.

56. A process as recited in claim 55 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

57. A process as recited in claim 56 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

58. A process for isomerizing saturated hydrocarbons comprising contacting a hydrocarbon feed comprising at least one saturated hydrocarbon under isomerization conditions with the catalyst system of claim 5.

59. A process as recited in claim 58 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

60. A process as recited in claim 59 wherein said isomerization conditions include the presence of carbon tetrachloride and a gas comprising hydrogen, a temperature in the range of from about 80C to about 260° C., a pressure in the range of from about atmospheric to about 1500 psig, and a WHSV from exceeding 0 hour$^{-1}$ to about 1000 hour$^{-1}$.

61. A process for isomerizing saturated hydrocarbons comprising contacting a hydrocarbon feed comprising at least one saturated hydrocarbon under isomerization conditions with the catalyst system of claim 6.

62. A process as recited in claim 61 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

63. A process as recited in claim 62 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

64. A process for isomerizing saturated hydrocarbons comprising contacting a hydrocarbon feed comprising at least one saturated hydrocarbon under isomerization conditions with the catalyst system of claim 7.

65. A process as recited in claim 64 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

66. A process as recited in claim 65 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

67. A process for isomerizing saturated hydrocarbons comprising contacting a hydrocarbon feed comprising at least one saturated hydrocarbon under isomerization conditions with the catalyst system of claim 8.

68. A process as recited in claim 67 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

69. A process as recited in claim 68 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

70. A process for isomerizing saturated hydrocarbons comprising contacting a hydrocarbon feed comprising at least one saturated hydrocarbon under isomerization conditions with the catalyst system of claim 9.

71.A process as recited in claim 70, wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

72. A process as recited in claim 71 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

73. A process for isomerizing saturated hydrocarbons comprising contacting a hydrocarbon feed comprising at least one saturated hydrocarbon under isomerization conditions with the catalyst system of claim 10.

74. A process as recited in claim 73 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

75. A process as recited in claim 74 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

76. A process for isomerizing saturated hydrocarbons comprising contacting a hydrocarbon feed comprising at 77. A process as recited in claim 76 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

78. A process as recited in claim 77 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

79. A process for isomerizing saturated hydrocarbons comprising contacting a hydrocarbon feed comprising at least one saturated hydrocarbon under isomerization conditions with the catalyst system of claim 12.

80. A process as recited in claim 79, wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

81. A process as recited in claim 80, wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

82. A process for isomerizing saturated hydrocarbons comprising contacting a hydrocarbon feed comprising at least one saturated hydrocarbon under isomerization conditions with the catalyst system of claim 13.

83. A process as recited in claim 82 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

84. A process as recited in claim 83 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

85. A process for isomerizing saturated hydrocarbons comprising contacting a hydrocarbon feed comprising at least one saturated hydrocarbon under isomerization conditions with the catalyst system of claim 14.

86. A process as recited in claim 85 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

87. A process as recited in claim 86 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

88. A process for isomerizing saturated hydrocarbons comprising contacting a hydrocarbon feed comprising at least one saturated hydrocarbon under isomerization conditions with the catalyst system of claim 15.

89. A process as recited in claim 88 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

90. A process as recited in claim 89 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

91. A process for isomerizing saturated hydrocarbons comprising contacting a hydrocarbon feed comprising at least one saturated hydrocarbon under isomerization conditions with the catalyst system of claim 16.

92. A process as recited in claim 91 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

93. A process as recited in claim 92 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

94. A process for isomerizing saturated hydrocarbons comprising contacting a hydrocarbon feed comprising at least one saturated hydrocarbon under isomerization conditions with a catalyst system prepared by the method of claim 20.

95. A process as recited in claim 94 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

96. A process as recited in claim 95 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

97. A process for isomerizing saturated hydrocarbons comprising contacting a hydrocarbon feed comprising at least one saturated hydrocarbon under isomerization conditions with a catalyst system prepared by the method of claim 22.

98. A process as recited in claim 97 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

99. A process as recited in claim 98 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

100. A process for isomerizing saturated hydrocarbons comprising contacting a hydrocarbon feed comprising at least one saturated hydrocarbon under isomerization conditions with a catalyst system prepared by the method of claim 23.

101. A process as recited in claim 100 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

102. A process as recited in claim 101 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

103. A process for isomerizing saturated hydrocarbons comprising contacting a hydrocarbon feed comprising at least one saturated hydrocarbon under isomerization conditions with a catalyst system prepared by the method of claim 24.

104. A process as recited in claim 103 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

105. A process as recited in claim 104 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

106. A process for isomerizing saturated hydrocarbons comprising contacting a hydrocarbon feed comprising at least one saturated hydrocarbon under isomerization conditions with a catalyst system prepared by the method of claim 25.

107. A process as recited in claim 106 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

108. A process as recited in claim 107 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

109. A process for isomerizing saturated hydrocarbons comprising contacting a hydrocarbon feed comprising at least one saturated hydrocarbon under isomerization conditions with a catalyst system prepared by the method of claim 26.

110. A process as recited in claim 109 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

111. A process as recited in claim 110 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

112. A process for isomerizing saturated hydrocarbons comprising contacting a hydrocarbon feed comprising at least one saturated hydrocarbon under isomerization conditions with a catalyst system prepared by the method of claim 27.

113. A process as recited in claim 112 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

114. A process as recited in claim 113 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

115. A process for isomerizing saturated hydrocarbons comprising contacting a hydrocarbon feed comprising at least one saturated hydrocarbon under isomerization conditions with a catalyst system prepared by the method of claim 28.

116. A process as recited in claim 115 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

117. A process as recited in claim 116 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

118. A process for isomerizing saturated hydrocarbons comprising contacting a hydrocarbon feed comprising at least one saturated hydrocarbon under isomerization conditions with a catalyst system prepared by the method of claim 29.

119. A process as recited in claim 118 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

120. A process as recited in claim 119 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

121. A process for isomerizing saturated hydrocarbons comprising contacting a hydrocarbon feed comprising at least one saturated hydrocarbon under isomerization conditions with a catalyst system prepared by the method of claim 30.

122. A process as recited in claim 121 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

123. A process as recited in claim 122 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

124. A process for isomerizing saturated hydrocarbons comprising contacting a hydrocarbon feed comprising at least one saturated hydrocarbon under isomerization conditions with a catalyst system prepared by the method of claim 31.

125. A process as recited in claim 124 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

126. A process as recited in claim 125 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

127. A process for isomerizing saturated hydrocarbons comprising contacting a hydrocarbon feed comprising at least one saturated hydrocarbon under isomerization conditions with a catalyst system prepared by the method of claim 32.

128. A process as recited in claim 127 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

129. A process as recited in claim 128 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

130. A process for isomerizing saturated hydrocarbons comprising contacting a hydrocarbon feed comprising at least one saturated hydrocarbon under isomerization conditions with a catalyst system prepared by the method of claim 33.

131. A process as recited in claim 130 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

132. A process as recited in claim 131 herein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

133. A process for isomerizing saturated hydrocarbons comprising contacting a hydrocarbon feed comprising at least one saturated hydrocarbon under isomerization conditions with a catalyst system prepared by the method of claim 34.

134. A process as recited in claim 133 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

135. A process as recited in claim 134 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

136. A process for isomerizing saturated hydrocarbons comprising contacting a hydrocarbon feed comprising at least one saturated hydrocarbon under isomerization conditions with a catalyst system prepared by the method of claim 35.

137. A process as recited in claim 136 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

138. A process as recited in claim 137 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

139. A process for isomerizing saturated hydrocarbons comprising contacting a hydrocarbon feed comprising at least one saturated hydrocarbon under isomerization conditions with a catalyst system prepared by the method of claim 36.

140. A process as recited in claim 134 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

141. A process as recited in claim 140 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

142. A process for isomerizing saturated hydrocarbons comprising contacting a hydrocarbon feed comprising at least one saturated hydrocarbon under isomerization conditions with a catalyst system prepared by the method of claim 37.

143. A process as recited in claim 142 wherein said at least one saturated hydrocarbon is selected from the group consisting of normal butane, normal pentane, normal hexane, normal heptane, normal octane, cyclohexane, methylpentane, methylcyclopentane, dimethylcyclopentane, cycloheptane, methylcyclohexane, methylcycloheptane, and combinations of any two or more thereof.

144. A process as recited in claim 143 wherein said isomerization conditions include the presence of carbon tetrachloride and a gas comprising hydrogen, a temperature in the range of from about 80° C. to about 260° C., a pressure in the range of from about atmospheric to about 1500 psig, and a WHSV from exceeding 0 hour$^{-1}$ to about 1000 hour$^{-1}$.

* * * * *

UNITED STATES PATENT AND TRADEMARK OFFICE
CERTIFICATE OF CORRECTION

PATENT NO.  : 6,090,992
DATED       : July 18, 2000
INVENTOR(S) : An-hsiang Wu and Charles A. Drake It is certified that error appears in the above-identified patent and that said Letters Patent is hereby corrected as shown below:

Claim 140, Column 18,
Line 34, please delete 134 and insert therefore -- 139 --.

Signed and Sealed this

Twenty-eighth Day of August, 2001

Attest:

NICHOLAS P. GODICI
Attesting Officer    Acting Director of the United States Patent and Trademark Office